(12) United States Patent
Yamamoto et al.

(10) Patent No.: US 6,994,987 B1
(45) Date of Patent: Feb. 7, 2006

(54) PROCESS FOR PRODUCING TRIPEPTIDES

(75) Inventors: Naoyuki Yamamoto, Sagamihara (JP); Keita Ueno, Machida (JP); Masahiro Ejiri, Machida (JP)

(73) Assignee: Calpis Co., Ltd., Tokyo (JP)

( * ) Notice: Subject to any disclaimer, the term of this patent is extended or adjusted under 35 U.S.C. 154(b) by 267 days.

(21) Appl. No.: 10/129,471

(22) PCT Filed: Nov. 10, 2000

(86) PCT No.: PCT/JP00/07930

§ 371 (c)(1),
(2), (4) Date: May 3, 2002

(87) PCT Pub. No.: WO01/34828

PCT Pub. Date: May 17, 2001

(30) Foreign Application Priority Data

Nov. 11, 1999 (JP) .......................................... 11/321084

(51) Int. Cl.
*C12P 21/06* (2006.01)
*C12N 1/20* (2006.01)

(52) U.S. Cl. ................. 435/68.1; 424/93.45; 435/252.9
(58) Field of Classification Search ................ 435/68.1, 435/252.9; 424/93.45
See application file for complete search history.

(56) References Cited

U.S. PATENT DOCUMENTS

| | | |
|---|---|---|
| 3,846,560 A | 11/1974 | Hempenius et al. |
| 3,876,806 A | 4/1975 | Hempenius et al. |
| 4,107,334 A | 8/1978 | Jolly |
| 4,293,571 A | 10/1981 | Olofsson et al. |
| 4,585,757 A | 4/1986 | Pang et al. .................... 514/18 |
| 4,687,739 A | 8/1987 | Sugisawa et al. |
| 4,687,840 A | 8/1987 | Pang et al. ................. 530/331 |
| 5,238,921 A | 8/1993 | Maruyama et al. ........... 514/18 |
| 5,314,873 A | 5/1994 | Tomita et al. ................ 514/21 |
| 5,409,718 A | 4/1995 | Klaver et al. .................. 426/42 |
| 5,418,218 A | 5/1995 | Wilber ........................ 514/11 |
| 5,466,472 A | 11/1995 | Kuma et al. .................. 426/43 |
| 5,486,461 A | 1/1996 | Nielsen ..................... 435/68.1 |
| 5,547,687 A | 8/1996 | Outinen et al. |
| 5,618,689 A | 4/1997 | McCarthy et al. |
| 5,656,268 A | 8/1997 | Sorodsky ................. 424/93.45 |
| 6,214,585 B1 | 4/2001 | Kwon et al. ............... 435/71.2 |
| 6,221,423 B1 | 4/2001 | Cho et al. .................... 426/656 |
| 6,372,282 B1 | 4/2002 | Edens et al. ................ 426/656 |
| 2002/0132288 A1 | 9/2002 | Swamylingappa et al. . 435/68.1 |
| 2002/0182301 A1 | 12/2002 | Draaisma et al. ........... 426/583 |
| 2003/0027769 A1 | 2/2003 | Scialdone et al. ............ 514/18 |
| 2003/0040475 A1 | 2/2003 | Toba et al. .................... 514/12 |
| 2003/0072863 A1 | 4/2003 | Hayasawa et al. .......... 426/580 |

FOREIGN PATENT DOCUMENTS

| | | |
|---|---|---|
| EP | 1 016 709 A1 | 7/2000 |
| EP | 1016709 | 7/2000 |
| EP | 10.18341 | 7/2000 |
| EP | 1 018 341 A1 | 7/2000 |
| JP | 59-44323 | 3/1984 |
| JP | 6-41191 A1 | 2/1994 |
| JP | 10-212245 | 8/1998 |
| JP | 99/16461 | 4/1999 |
| JP | 99/16862 | 4/1999 |
| WO | WO 01/68113 A1 | 9/2001 |
| WO | WO 01/68114 A1 | 9/2001 |

OTHER PUBLICATIONS

Biosciences and Industry, Susumu Maruyama, "Production of Hypotensive Peptides from Food Protein", 47 No. 11, 38–42, 1989. (with partial translation).
Japan Fermentation Engineering Society, Susumu Maruyama, et al. "Production of Peptide Inhibitors of the Renin–Angiotensin System from Maize Protein", p. 23, 1988.
Japanese Society for Bioscience, Biotechnology and Agro-chemistry, Susumu Maruyama, et al., "Angiotensin Converting Enzyme Inhibitory Effect and Hypotensive Effect of Peptides from Repeat Sequence Region of Corn Seed Protein", p. 8, 1989.
Japan Nutrition and Food Society, Shinsuke Miyoshi, et al., "Hypotensive Effect of Enzymolytic Product of Maize Protein on SHR", p. 113, 1989.
Journal of Japan Agricultural Chemistry Society, Shinsuke Miyoshi, et al., "Angiotensin Converting Enzyme Inhibitory Effect of Peptides Derived from Maize Protein", 64(3), 555, 1990. (translation).
Antonie van Leeuwenhoek, "The Proteolytic Systems of Lactic Acid Bacteria," 70: 187–221. 1996.
Patent Abstracts of Japan, vol. 018, No. 268, Publication No. 06041191, Publication Date Feb. 15, 1994, Calpis Food Ind. Co., Ltd.
Cunningham, et al., "Proline specific peptidases", Biochimica et Biophysica Acta 1343 (1997), pp. 160–186, Dec. 5, 1997.
Y. Nakamura et al., "Purification and characterization of Angiotensin I–converting enzyme inhibitors from sour milk" Journal of Dairy Science, vol. 78, No. 4, 1995, pp. 777–783.
Y. Nakamura et al., "Antihypertensive effect of sour milk and peptides isolated from it that are inhibitors to Angiotension I–converting enzyme" Journal of Dairy Science, vol. 78, No. 6, 1995, pp. 1253–1257.
A. Abubakar et al., "Structural analysis of new antihypertensive peptides derived from cheese whey protein by proteinase K digestion" Journal of Dairy Science, vol. 81, No. 12, 1998, pp. 3131–3138.

*Primary Examiner*—Herbert J. Lilling
(74) *Attorney, Agent, or Firm*—Darby & Darby

(57) ABSTRACT

A process for efficiently, easily and stably producing tripeptides Val-Pro-Pro and Ile-Pro-Pro, which are useful as hypotensive drugs, anti-stress drugs, etc., by an enzymatic method. This process involves the step of cleaving a milk casein-containing material with a proteinase to form an intermediate peptide selected from the group consisting of a peptide containing the sequence Val-Pro-Pro but having no Pro other than this sequence, a peptide containing the sequence Ile-Pro-Pro but having no Pro other than this sequence, and a mixture of these peptides, and then cleaving the intermediate peptide with a peptidase to thereby give at least one of the tripeptides Val-Pro-Pro and Ile-Pro-Pro.

14 Claims, No Drawings

US 6,994,987 B1

PROCESS FOR PRODUCING TRIPEPTIDES

FIELD OF ART

The present invention relates to a method for producing a tripeptide by which tripeptides Val-Pro-Pro and/or Ile-Pro-Pro may be produced efficiently.

BACKGROUND ART

It is known in the prior art that various peptides having specific sequences have various physiological activities. Examples of such peptides include tripeptides Val-Pro-Pro and Ile-Pro-Pro. These tripeptides may be found in a milk fermented with lactic acid bacteria and are known to have a strong angiotensin converting enzyme (referred to hereinbelow as ACE) inhibitory activity, and show a strong anti-hypertensive activity on spontaneous hypertension rats (SHR), as well as anti-hypertensive effect on hypertensive patients (J. Dairy Sci. 1995, 78:777–783; J. Dairy Sci. 1995, 78:1253–1257; Am. J. Clin. Nutr. 1996, 64:767–771). Further, it is reported that the tripeptides Val-Pro-Pro and Ile-Pro-Pro also have an anti-stress activity (JP-A-11-100328).

As methods for producing the tripeptides Val-Pro-Pro and/or Ile-Pro-Pro, an example of efficient production with lactic acid bacteria fermentation has been reported (JP-A-11-98978). However, lactic acid bacteria fermentation ceases before complete digestion because of low pH as a result of lactic acid fermentation, which results in a large amount of undigested casein. Further, the cultured liquid produced by the lactic acid bacteria fermentation contains a large amount of lactic acid which may cause disadvantage upon processing the cultured liquid into a variety of products. For example, the co-existing lactic acid prevents formation of powders, and it is thus required to remove acids from cultured liquid for forming powders.

Another possible method for producing the tripeptides is an enzymological method. Compared to the lactic acid fermentation method, the enzymological method is expected to have advantages such as improved yield of the peptides, stable production, reduced production steps and number of operating persons, and no generation of lactic acid. However, upon digesting proteins by the enzymological method for producing the tripeptides Val-Pro-Pro and/or Ile-Pro-Pro, digestion reactivity by peptidase is considerably low at amino acid sequences containing Pro such as Xaa Pro or Pro Xaa (Xaa represents any amino acid). Therefore, it is difficult to digest the sequence Pro-Xaa in production of the tripeptides Val-Pro-Pro and/or Ile-Pro-Pro by the enzymological method, and higher yield than that in lactic acid fermentation method has not been obtained with the enzymological method. For example, JP-A-11-100328 discloses a method in which milk casein is treated with proteinase and then with carboxypeptidase, as an example of the method for obtaining the tripeptides Val-Pro-Pro and/or Ile-Pro-Pro. However there is no disclosure of the specific treating steps. JP-A-11-100328 merely discloses in the Examples other methods than the enzymological method such as lactic acid fermentation.

As the method for producing useful peptides other than the tripeptides Val-Pro-Pro and/or Ile-Pro-Pro by digestion of proteins with the combination of proteinase and peptidase, there have been proposed a method for obtaining a tripeptide Leu-Pro-Pro having ACE inhibitory activity from gamma-zein (Japanese Patent No. 2873327), and a method for obtaining a peptide Tyr-Pro-Phe-Pro-Gly-Pro-Ile-Xaa-Asn from beta-casein (JP-A-6-128287). However, these method have not been made practicable because of insufficient yield and instability for industrial production.

DISCLOSURE OF INVENTION

The object of the present invention is to provide an industrially useful method for producing the tripeptides in which the tripeptides Val-Pro-Pro and/or Ile-Pro-Pro useful as anti-hypertensive agent or anti-stress agent may be produced stably and readily with high yield.

According to the present invention, there is provided a method for producing a tripeptide by digesting a material containing a milk casein with a proteinase and a peptidase to obtain at least one of tripeptides Val-Pro-Pro and Ile-Pro-Pro, the method including the steps of digesting the material containing the milk casein with the proteinase to produce an intermediate peptide selected from the group consisting of a peptide containing a sequence Val-Pro-Pro but containing no Pro other than those in this sequence, a peptide containing a sequence Ile-Pro-Pro but containing no Pro other than those in this sequence, and mixtures thereof, and digesting the intermediate peptide with the peptidase to produce at least one of the tripeptides Val-Pro-Pro and Ile-Pro-Pro.

PREFERRED EMBODIMENTS OF THE INVENTION

In the method for producing a tripeptide of the present invention, a material containing a milk casein is digested with a specific proteinase and peptidase to obtain a tripeptide Val-Pro-Pro and/or Ile-Pro-Pro.

The material containing the milk casein may be suitably selected considering the content of the specific tripeptide sequence, cost of the material, and readiness of industrial application. Examples thereof may include materials containing a milk casein such as beta casein and kappa casein, such as an animal milk, a skim milk, a powdered skim milk, a milk casein and processed products thereof.

Among some classes of caseins, beta casein and kappa casein contain the sequences Val-Pro-Pro and Ile-Pro-Pro. Therefore, the material containing the milk casein may preferably be those containing these caseins.

An ordinary milk casein contains 25 to 30 wt % of beta casein and 10 to 15 wt % of kappa casein, i.e., larger amount of beta casein than that of kappa casein. Therefore, the present production method may utilize beta casein as a dominant substrate.

The aforementioned specific proteinase is a proteinase which digests milk casein and produces the specific intermediate peptide.

The specific intermediate peptide is a peptide selected from the group consisting of a peptide containing a sequence Val-Pro-Pro but containing no Pro other than those in this sequence, a peptide containing a sequence Ile-Pro-Pro but containing no Pro other than those in this sequence, and mixtures thereof. That is, the specific intermediate peptide is a peptide containing a sequence Val-Pro-Pro but containing no Pro other than in this sequence, and/or a peptide containing a sequence Ile-Pro-Pro but containing no Pro other than in this sequence. Specifically, the intermediate peptide may include a peptide Gln Asn Ile Pro Pro Leu Thr Gln Thr, the sequence of which is a part of the sequence of beta casein, or one or more of peptides identical with peptides obtained by removing one or more amino acids from this peptide at amino terminus and/or carboxy terminus until the sequence becomes Ile-Pro-Pro (the following SEQ ID NO:

1×15), or a peptide Val Val Val Pro Pro Phe Leu Gln the sequence of which is a part of the sequence of beta casein, or one or more of peptides identical with peptides obtained by removing one or more amino acids from this peptide at amino terminus and/or carboxy terminus until the sequence becomes Val-Pro-Pro (the following SEQ ID NO: 16–27).

Gln Asn Ile Pro Pro Leu Thr Gln Thr (SEQ ID NO: 1)
    Asn Ile Pro Pro Leu Thr Gln Thr (SEQ ID NO: 2)
    Ile Pro Pro Leu Thr Gln Thr (SEQ ID NO: 3)
Gln Asn Ile Pro Pro Leu Thr Gln (SEQ ID NO: 4)
    Asn Ile Pro Pro Leu Thr Gln (SEQ ID NO: 5)
    Ile Pro Pro Leu Thr Gln (SEQ ID NO: 6)
Gln Asn Ile Pro Pro Leu Thr (SEQ ID NO: 7)
    Asn Ile Pro Pro Leu Thr (SEQ ID NO: 8)
    Ile Pro Pro Leu Thr (SEQ ID NO: 9)
Gln Asn Ile Pro Pro Leu (SEQ ID NO: 10)
    Asn Ile Pro Pro Leu (SEQ ID NO: 11)
    Ile Pro Pro Leu (SEQ ID NO: 12)
Gln Asn Ile Pro Pro (SEQ ID NO: 13)
    Asn Ile Pro Pro (SEQ ID NO: 14)
    Ile Pro Pro (SEQ ID NO: 15)
Val Val Val Pro Pro Phe Leu Gln (SEQ ID NO: 16)
    Val Val Pro Pro Phe Leu Gln (SEQ ID NO: 17)
    Val Pro Pro Phe Leu Gln (SEQ ID NO: 18)
Val Val Val Pro Pro Phe Leu (SEQ ID NO: 19)
    Val Val Pro Pro Phe Leu (SEQ ID NO: 20)
    Val Pro Pro Phe Leu (SEQ ID NO: 21)
Val Val Val Pro Pro Phe (SEQ ID NO: 22)
    Val Val Pro Pro Phe (SEQ ID NO: 23)
    Val Pro Pro Phe (SEQ ID NO: 24)
Val Val Val Pro Pro (SEQ ID NO: 25)
    Val Val Pro Pro (SEQ ID NO: 26)
    Val Pro Pro (SEQ ID NO: 27)

The proteinase may include papain, "PROTEASE A™" (manufactured by Amano Pharmaceutical Co., Ltd., Nagoya, Japan) "PROTEASE M™" (manufactured by Amano Pharmaceutical Co., Ltd., Nagoya, Japan) "PROTEASE P™" (manufactured by Amano Pharmaceutical Co., Ltd., Nagoya, Japan) or combinations thereof. "PROTEASE A™" and "PROTEASE M™" are derived from *Aspergillus oryzae*. "PROTEASE P™" is derived from *Aspergillus melleus*. "PROTEASE A™" is an enzymatic agent stable in the neutral range, and has a protease activity of not less than 10,000 units/g (ph 7.0, Amano method). "PROTEASE M™" is an enzymatic agent stable in the acid range, and has a protease activity of not less than 5,500 units/g (pH 3.0, Amano method). "PROTEASE P™" is an enzymatic agent stable in the neutral range, and has a protease activity of not less than 30,000 units/g (pH 8.0, Amano method).

The peptidase may include various peptidase capable of digesting the intermediate peptide that has been produced by the proteinase to generate the tripeptides Val-Pro-Pro and/or Ile-Pro-Pro. The peptidase does not necessarily have ability to directly digest casein. For example, an exopeptidase such as an amino peptidase and a carboxy peptidase; an endopeptidase such as an oligopeptidase, and mixtures thereof.

The peptidase may preferably include a carboxypeptidase and/or an endopeptidase that is capable of cleaving a bond between Pro and Xaa of the sequence Val-Pro-Pro-Xaa and/or Ile-Pro-Pro-Xaa. More specifically, the peptidase may preferably be capable of cleaving a bond Pro-Leu and/or Pro-Phe in sequences Ile-Pro-Pro-Leu and/or Val-Pro-Pro-Phe contained in the milk casein. The peptidase may preferably have specificity against these bonds.

The peptidase may suitably be selected in accordance with substrate specificity of the cooperatively used proteinase and other factors. For example, only one of either aminopeptidase or carboxypeptidase may be employed depending on the substrate specificity of the proteinase. However, it is generally preferable to use a combination of a peptidase which digests peptides from the N terminus such as aminopeptidase, and a peptidase which digests from the C terminus such as a carboxypeptidase and/or an oligopeptiase. Specifically, when papain, "PROTEASE A™" (manufactured by Amano Pharmaceutical Co., Ltd., Nagoya, Japan), "PROTEASE M™" (manufactured by Amano Pharmaceutical Co., Ltd., Nagoya, Japan), "PROTEASE P™" (manufactured by Amano Pharmaceutical Co., Ltd., Nagoya, Japan), or the mixtures thereof is employed as the proteinase, it is preferable to cooperatively use a combination of the aminopeptidase and the carboxypeptidase and/or oligopeptidase as the peptidases.

Examples of the aminopeptidases may include aminopeptidase I derived from *Streptomyces griseus* (manufactured by Sigma Chemical Co.), aminopeptidase derived from *Aeromonas proteolytica* (manufactured by Sigma Chemical Co.), leucine aminopeptidase derived from porcine kidney cytoplasm, and leucine aminopeptidase derived from porcin kidney endoplasmic reticulum.

Examples of the carboxypeptidases may include carboxypeptidase Y available from Sigma Chemical Co., St. Louis, Mo.), carboxypeptidase A available from Sigma Chemical Co., St. Louis, Mo.), carboxypeptidase B available from Sigma Chemical Co., St. Louis, Mo.), and cathepsin B (available from Sigma Chemical Co., St. Louis, Mo.).

Other than those exemplified above, examples of the peptidase may further include enzymes derived from microorganisms such as lactic acid bacteria, *Escherichia coli* bacteria, or *Bacillus subtilis* bacteria, or enzymes derived from an animal tissue or a plant. For example, a peptidase derived from lactic acid bacteria *Lactobacillus helveticus* may be used.

The peptidase derived from *Lactobacillus helveticus* may be obtained by collecting cell bodies by centrifugation from a cultured liquid in which the lactic acid bacteria have been cultured, crushing the cell bodies by cell grinding such as ultrasonic treatment, centrifuging for removing precipitate and collecting supernatant as a crude enzyme extract, and fractioning the crude extract with an adsorption separation column such as DEAE-sepharose (manufactured by Pharmacia Co.).

The peptidase derived from lactic acid bacteria *Lactobacillus helveticus* may be used without other peptidases for digestion of the intermediate peptide to obtain tripeptides Ile-Pro-Pro and/or Val-Pro-Pro with high yield. However, the peptidase derived from lactic acid bacteria *Lactobacillus helveticus* may be used with other peptidase such as the aminopeptidase and/or the carboxypeptidase.

The order for contacting the proteinase and the peptidase with the material containing the milk casein is not particularly limited as long as the material containing the milk casein may be digested with the proteinase to produce the intermediate peptide which may be digested with the peptidase to obtain the desired tripeptide. Examples of the procedures for bring the material into contact with the proteinase and the peptidase may include a procedure (a) including the steps of bringing the material containing the milk casein into contact with the proteinase to obtain the intermediate peptide, and then bringing the intermediate peptide into contact with the peptidase for performing the desired digestion; and a procedure (b) including the step of brining the material containing the milk casein into contact with the proteinase and the peptidase simultaneously, for performing desirable digestion of each enzyme.

In the procedure (a), preferable ratio of the proteinase to the material containing milk casein may be 1/100 to 1/10000. The condition for digesting the milk casein with the proteinase to produce the intermediate peptide may usually be at pH 5 to 9, at the temperature of 20 to 40° C., and preferably at the optimum pH and temperature of the enzyme, for 3 to 24 hours.

After obtaining the intermediate peptide and before the intermediate peptide is contacted with the peptidase in the procedure (a), various operation may optionally be performed such as inactivation of proteinase, removal of the unreacted protein, elevation of the intermediate peptide concentration, and removal of the solvent.

The inactivation of the proteinase may usually be effected by heating treatment at 60 to 100° C. Such an inactivation may increase efficiency of the subsequent digestion with the peptidase.

The removal of the unreacted protein may be effected by e.g., centrifugation at 5000 to 20000 rpm for 3 to 10 minutes and removal of the precipitate.

The elevation of the intermediate peptide concentration may be performed with a hydrophobic resin. Examples of the hydrophobic resin may include silica resin to which a group containing cyano group such as propionitrile group, phenyl group, or an alkyl group having 1 to 18 carbon atoms is bound. More specifically, the hydrophobic resin may be "Amberlite XAD-7", "Amberlite XAD-2" (trade name, manufactured by Organo Corporation), and "Sep-Pak Cartridge" (manufactured by Waters Corporation). Elevation of the intermediate peptide concentration may be effected by making the resin adsorb the intermediate peptide in accordance with a column method or a batch method, and then eluting the intermediate peptide with a solvent such as a polar solvent such as methanol, ethanol, 1-propanol, 2-propanol and acetonitrile.

The removal of the solvent may be effected by a vacuum concentration treatment.

In the procedure (a), condition for performing desired digestion by contacting the intermediate peptide with the peptidase may be at pH 4.0 to 7.0 and preferably at pH 4.5 to 6.5 and at the temperature of 25 to 40° C. and preferably 30 to 45° C. When a plurality of enzymes are employed as the peptidases, a plurality of the reactions may separately be performed at the optimum condition of each enzyme.

In the procedure (b), the preferable condition for the desired digestion when the proteinase and the peptidase are simultaneously contacted with the material containing the milk casein may be at pH 4.5 to 7.0 and at the temperature of 25 to 50° C.

In the production method of the present invention, the reaction mixture after performing the digestion with the proteinase and the peptidase may usually contain tripeptides Val-Pro-Pro and Ile-Pro-Pro as well as other peptides. The reaction mixture itself may be the product. Alternatively, the reaction mixture may be subject to concentration and purification of the tripeptides Val-Pro-Pro and Ile-Pro-Pro, to obtain the product. The tripeptides Val-Pro-Pro and Ile-Pro-Pro may be made in the form of an industrially acceptable salt such as a salt of hydrochloric acid, succinic acid, citric acid and tartartic acid.

A product containing the tripeptides obtainable through the present production method itself or the product which has further been admixed with other materials for food or medicaments to be in the form of liquid, powders, granules or tablets may be used as a dairy product such as yogurt and milk beverage, general foods and beverages, foods for specified health use, health foods and medicaments having hypotensive effect and anti-stress effect.

With the present method for producing the tripeptide, the tripeptides Val-Pro-Pro and Ile-Pro-Pro that are useful as hypotensive agent or anti-stress agent may be produced readily and stably with high yield by the enzymological method. Therefore, the present method has a notable industrial value.

EXAMPLES OF THE INVENTION

The present invention will be explained in further detail with reference to the Experiments and Examples. However, the present invention is not limited thereto.

Experiments 1-1 to 1-21

Study on the Selection of the Optimum Peptidase Formulation and Optimum Reaction Conditions for Producing Tripeptides Ile-Pro-Pro and Val-Pro-Pro from the Intermediate Peptides Peptides shown in Table 1 were chemically synthesized. These are the synthetic peptides based on the amino acid sequence of beta casein containing the sequence Ile-Pro-Pro and Val-Pro-Pro in the amino sequence thereof and do not have Pro in other part than these sequences. All of these synthetic peptides were synthesized with the automatic peptide synthesizing machine PPSM-8 (manufactured by Shimadzu Corporation).

Enzymological reactivity of various commercially available peptidase formulations against the peptides shown in Table 1 was then examined. Each synthetic peptide was dissolved at the concentration of 10 $\mu$g/ml in 100 mM phosphate buffer pH 5.3 as to Experiments 1-1 to 1-4, 1-10 to 1-12, 1-16 and 1-21, or in 50 mM Tris-HCl buffer pH 8.0 as to other Experiments. Each of various peptidase formulations shown in Table 1 was then added so that the concentration thereof became 0.01 $\mu$g/ml, and the reaction was performed at 37° C. for 3 hours. After the enzyme reaction, the mixture was analyzed by the reverse phase high performance liquid chromatography (HPLC). A peak at retention time of 11.0 min. attributed to the tripeptide Val-Pro-Pro and a peak at retention time 13.7 min. attributed to the tripeptide Ile-Pro-Pro were detected. The fractions of the detected peak were collected and amino acid sequence analysis was performed by the automatic peptide analyzer model PPSQ-10 (manufactured by Shimadzu Corporation). The analysis revealed that the amino acid sequences of the peptides in the collected peaks were Ile-Pro-Pro and Val-Pro-Pro. HPLC analysis conditions are shown below:

Pump: L6200 Intelligent Pump and L6000 Pump (manufactured by Hitachi, Ltd.)

Detector: L4000 UV Detector (manufactured by Hitachi, Ltd.)

Column: Microbondasphere 5 $\mu$C18 (100 3.9×150 mm, manufactured by Waters Corporation)

Eluents: Eluent A: aqueous solution containing 0.1 wt % trifluoroacetic acid (TFA)

Eluent B: acetonitrile containing 0.1 wt % trifluoroacetic acid

Elution condition: linear gradient elution (40 minutes) from Eluent B 0% (Eluent A 100%) to Eluent B 40% (Eluent A 60%).

Flow rate: 1 ml/min.

TABLE 1

| Experiment | Sequence of synthetic peptides | Amino-peptidase | Carboxy-peptidase | Existence of IPP or VPP peaks |
|---|---|---|---|---|
| 1-1 | Asn Ile Pro Pro Leu | A | Y | IPP |
| 1-2 | Asn Ile Pro Pro Leu | LC | Y | IPP |
| 1-3 | Asn Ile Pro Pro Leu | LM | Y | IPP |
| 1-4 | Asn Ile Pro Pro Leu | I | Y | IPP |
| 1-5 | Asn Ile Pro Pro Leu | A | B | — |
| 1-6 | Asn Ile Pro Pro Leu | LC | B | — |
| 1-7 | Asn Ile Pro Pro Leu | LM | B | — |
| 1-8 | Asn Ile Pro Pro Leu | I | B | — |
| 1-9 | Asn Ile Pro Pro Leu | A | A | — |
| 1-10 | Ile Pro Pro Leu Thr Gln Thr | — | Y | IPP |
| 1-11 | Gln Asn Ile Pro Pro Leu Thr Gln Thr | I | Y | IPP |
| 1-12 | Val Pro Pro Phe | — | Y | VPP |
| 1-13 | Val Pro Pro Phe | — | B | — |
| 1-14 | Val Pro Pro Phe | — | A | — |
| 1-15 | Val Pro Pro Phe | — | G | — |
| 1-16 | Val Pro Pro Phe Leu Gln | — | Y | VPP |
| 1-17 | Val Val Pro Pro | A | — | VPP |
| 1-18 | Val Val Pro Pro | LC | — | VPP |
| 1-19 | Val Val Pro Pro | LM | — | VPP |
| 1-20 | Val Val Pro Pro | I | — | VPP |
| 1-21 | Val Val Val Pro Pro Phe Leu Gln | I | Y | VPP |

Acronyms of the enzymes in Table 1 refer to the following enzymes:

<Aminopeptidases>

A: Aminopeptidase (manufactured by Sigma Chemical Co., St. Louis, Mo.)

LC: Leucine aminopeptidase, cytosol (aminopeptidase derived from porcine kidney cytoplasm, manufactured by Sigma Chemical Co., St. Louis, Mo.)

LM: Leucine aminopeptidase, microsomal (aminopeptidase derived from porcine kidney enodplasmic reticulum, manufactured by Sigma Chemical Co., St. Louis, Mo.)

I: Aminipeptidase I (manufactured by Sigma Chemical Co., St. Louis, Mo.)

<Carboxypeptidases>

Y: Carboxypeptidase Y (manufactured by Sigma Chemical Co., St. Louis, Mo.)

B: Carboxypeptidase B (manufactured by Sigma Chemical Co., St. Louis, Mo.)

A: Carboxypeptidase A (manufactured by Sigma Chemical Co., St. Louis, Mo.)

G: Cathepsin G (manufactured by Sigma Chemical Co., St. Louis, Mo.)

As shown in Table 1, every amino peptidase removes amino acids at amino terminus preserving one amino acid which locates at amino terminus side of the Pro residue. When carboxy peptidase Y was brought into reaction at pH 5.3, it was recognized that the enzyme is capable of effectively cleave the bond between Pro and Leu in Pro-Pro-Leu and the bond between Pro and Phe in Pro-Pro-Phe.

When the longer peptide Gln-Asn-Ile-Pro-Pro-Leu-Thr-Gln-Thr and Val-Val-Val-Pro-Pro-Phe-Leu-Gln were subjected to the enzyme treatment with aminopeptidase and carboxypeptidase Y (Experiments 1-11 and 1-21), the production of the tripeptides Ile-Pro-Pro or Val-Pro-Pro was also recognized. That is, it was confirmed that the tripeptides Ile-Pro-Pro and/or Val-Pro-Pro may be produced by cooperatively bringing an aminopeptidase and a carboxypeptidase into reaction with a peptide having a sequence identical with a part of casein sequence and containing the sequence Ile-Pro-Pro or Val-Pro-Pro therein but containing no Pro other than these sequences.

Experiment 2

Production of the Intermediate Peptides with Proteinase

A peptide consisting of 28 amino acids and having a sequence identical with a part of casein sequence and containing the sequence Ile-Pro-Pro and Val-Pro-Pro therein was chemically synthesized by the automatic peptide synthesizer model PPSQ-10. The sequence of the peptide synthesized is as follows: Leu Pro Gln Asn Ile Pro Pro Leu Thr Gln Thr Pro Val Val Val Pro Pro Phe Leu Gln Pro Glu Val Met Gly Val Ser Lys (SEQ ID NO: 28)

This synthetic peptide was reacted with various commercially available proteinase formulations, seeking for a proteinase capable of producing a peptide containing the sequence Ile-Pro-Pro or Val-Pro-Pro therein but containing no Pro other than these sequences.

That is, 0.1 μg/ml of each enzyme was added to 10 μg/ml of the synthetic peptide (in 100 mM phosphate buffer pH 6.1). The mixture was reacted at 37° C. for 5 hours to obtain a reacted liquid. The reacted liquid was analyzed by the reverse phase high performance liquid chromatography (HPLC). The fractions of the detected peptide peaks were collected and amino acid sequence analysis was performed by the automatic peptide analyzer model PPSQ-10.

As a result, it was confirmed that a peptide Val-Pro-Pro-Phe-Leu as the peptide containing the sequence Val-Pro-Pro, and peptides Asn-Ile-Pro-Pro-Leu-Thr and Ile-Pro-Pro-Leu-Thr as the peptide containing the sequence Ile-Pro-Pro were produced in the reaction mixture when papain (manufactured by Sigma Chemcial Co.) was employed.

Experiment 3

Treatment of the Intermediate Peptide with the Peptidase

The reacted liquid produced with paparin as the proteinase in Experiment 2 was heated at 100° C. for 5 minutes, to inactivate the proteinase. Aminopeptidase A (manufactured by Sigma Chemical Co.) was added to the mixture at 0.1 μg/ml, and reacted at 37° C. for 3 hours. After completing the reaction, 1N hydrochloric acid was added for adjusting pH to 5.3. Carboxypeptidase Y was added to the mixture at 0.1 µg/ml, and the mixture was further reacted at 37° C. for 10 hours. The resulting reacted liquid was analyzed by the reverse phase high performance liquid chromatography (HPLC) under the same conditions as in Experiment 1. As a result, peptide peaks which appear to be of the tripeptides Val-Pro-Pro and Ile-Pro-Pro were detected. The fractions of the detected peaks were collected and amino acid sequence analysis was performed by the automatic peptide analyzer model PPSQ-10. It was confirmed these peaks were of the tripeptides Ile-Pro-Pro and Val-Pro-Pro.

Experiment 4

Screening of Lactic Acid Bacteria Peptidases Producing the Tripeptides Ile-Pro-Pro and Val-Pro-Pro from the Intermediate Peptide Peptidases derived from the lactic acid bacteria *Lactobacillus helveticus* were screened in accordance with the following operation seeking for a peptidase that may be employed for the present invention.
(Extraction and fractionation of the enzymes from *Lactobacillus helveticus*)

A milk medium containing 9 wt % skim milk was inoculated with lactic acid bacteria *Lactobacillus helveticus* CM4 strain (deposited at National Institute of Bioscience and Human-Technology (1–3, Higashi 1 chome Tsukuba-shi Ibaraki-ken 305, Japan) under deposition number FEFM BP-6060 on Aug. 15, 1997) (referred to hereinbelow as CM4 strain). The bacteria were cultured at 37° C. for 24 hours. The CM4 strain has been accorded the aforementioned accession number under the Budapest Treaty on the International Recognition of the Deposit of Microorganisms for the Purposes of Patent Procedure. All restrictions on the availability to the public of this strain will be irrevocably removed upon the granting of a patent. To 500 ml of a fresh 9 wt % milk medium, cultured mixture was added at 5 wt %. PH start culturing was performed at 37° C. and at the pH of 6.5. Five hours after the start of pH stat culturing, sodium citrate was added so that the final concentration thereof became 2 wt %. The mixture was stirred for 30 minutes at room temperature. After confirming that the cultured liquid became clear, cell bodies were collected by centrifugation at 5000 g for 10 minutes. The cell bodies were washed twice with 50 mM phosphate buffer containing 150 mM NaCl pH 6.8, and suspended in 20 ml of 50 mM tris-Cl pH 8.0, and then crushed with an ultrasonic crusher (model 5203, manufactured by Ohtake Works Co.). Centrifugation at 15000 g was performed for 10 minutes for removing the precipitant and collecting the supernatant as a crude extract. 5 ml of the crude extract was passed through 1 ml of DEAE-sepharose column (manufactured by Pharmacia Corporation) that has been pre-equilibrated with the tris buffer. The column was washed with 5 ml of the tris buffer and then sequentially washed with 3 ml of tris buffers containing 50 mM, 100 mM, 150 mM, 200 mM, 300 mM and 500 mM NaCl, for fractionation. As a result, six fractions (fractions 1 to 6) was obtained as shown in Table 2.
(Digestion of the Intermediat Peptide)

An intermediate peptide Val-Pro-Pro-Phe-Leu was chemically synthesized. The synthesized peptide was dissolved at 10 µg/ml in 100 mM phosphate buffer (pH 6.1). This solution and one of the fractions 1 to 6 were mixed at the volume ratio of 9:1, and reacted at 37° C. for 30 minutes. After finishing the reaction, the reacted liquid was analyzed by the reverse phase high performance liquid chromatography (HPLC) to confirm generation of tripeptide Val-Pro-Pro. The amount of the produced tripeptide Val-Pro-Pro was calculated as a relative amount by multiplying the height of the peak (mm) of the tripeptide Val-Pro-Pro detected at the HPLC retention time of 11.0 min. by the volume of the eluent (ml). The results are shown in Table 2.

TABLE 2

| Fraction | NaCl concentration in the buffer (mM) | Volume (ml) | Amount of VPP produced (relative amount) |
| --- | --- | --- | --- |
| Washing liquid | 0 | 5 | 0 |
| 1 | 50 | 3 | 0 |
| 2 | 100 | 3 | 6.5 |
| 3 | 150 | 3 | 12 |
| 4 | 200 | 3 | 45 |
| 5 | 300 | 3 | 12 |
| 6 | 500 | 3 | 0 |

As a result, a peptide peak showing the peptidase activity producing the tripeptide Val-Pro-Pro was recognized in the analysis of a liquid reacted with the fractions 2 to 5. These fractions contained an endopeptidase involved in reaction for producing the tripeptide Val-Pro-Pro from the peptide Val-Pro-Pro-Phe-Leu. Particularly, the fraction 4 contained approximately 0.01 µg of the endopeptidase.

Subsequently, the fraction 4 having the strongest peptidase activity was reacted with other chemically synthesized intermediate peptides as substrates, and the reacted liquid was analyzed by the HPLC for detecting generation of the tripeptide Ile-Pro-Pro or Val-Pro-Pro in the same manner as the above. As a result, it was confirmed that the tripeptide Val-Pro-pro was produced from the peptides Val-Pro-Pro-Phe-Leu and Val-Pro-Pro-Phe-Leu-Gln. Further, it was confirmed that the tripeptide Ile-Pro-Pro was produced from the peptides Ile-Pro-Pro-Leu-Thr-Gln-Thr and Ile-Pro-Pro-Leu-Thr. The results are shown in Table 3.

TABLE 3

| Substrate peptide | Peptide produced |
| --- | --- |
| Val Pro Pro Phe Leu Gln Pro Glu (SEQ ID NO: 29) | — |
| Val Pro Pro Phe Leu Gln | Val Pro Pro |
| Val Pro Pro Phe Leu | Val Pro Pro |
| Ile Pro Pro Leu Thr Gln Thr | Ile Pro Pro |
| Ile Pro Pro Leu Thr | Ile Pro Pro |

Experiment 5

Production of the Tripeptide Ile-Pro-Pro and Val-Pro-Pro with the Combination of the Proteinase and the Peptidase Enzyme derived from *L. helveticus*

To 10 µg/ml of the synthetic peptide consisting of the 28 amino acids that is the same as the one used in Experiment 2 (in 100 mM phosphate buffer pH 6.1), each of the commercially available proteinase enzymes for food processing shown in Table 4 was added at 0.1 µg/ml. The mixture was reacted at 37° C. for 5 hours. After finishing the reaction, the reacted liquid was heated at 100° C. for 5 minutes for inactivating the proteinase, and then reacted with the fraction 4 obtained in Experiment 4. The resulting reaction mixture was then analyzed by HPLC for detecting the production of the tripeptides Ile-Pro-Pro or Val-Pro-Pro. Existence of the tripeptide in each of the reacted liquid are shown in Table 4.

TABLE 4

| Enzyme | Origin | Production of the tripeptides Ile-Pro-Pro and Val-Pro-Pro |
|---|---|---|
| Trypsin (Type I)[1] | bovine pancreas | No |
| Type XXIII[1] | Aspergillus oryzae | No |
| Pepsin[1] | Porcine Stomach Mucosa | No |
| Subtilisin Carlsberg[1] | Bacillus licheniformis | No |
| Subtilisin BPN[1] | Bacillus amyloliquefaciens | No |
| V8 Protease[1] | Staphylococcus aureus | No |
| Papain[1] | Papaya Latex | Yes |
| "PROTEASE A ™"[2] | Aspergillus oryzae | Yes |
| "PROTEASE M ™"[2] | Aspergillus oryzae | Yes |
| "PROTEASE N ™"[2] | Bacillus subtilis | No |
| "PROTEASE P ™"[2] | Aspergillus melleus | Yes |
| "PROTEASE S ™"[2] | Bacillus sp. | No |
| Nucleicin[3] | Bacillus subtilis | No |
| Orientase ONS[3] | Aspergillus oryzae | No |
| Orientase 10NL[3] | Bacillus subtilis | No |
| Orientase 90N[3] | Bacillus subtilis | No |

[1] manufactured by Sigma Chemical Co., St. Louis, MO
[2] manufactured by Amano Pharmaceutical Co., Ltd., Nagoya, Japan
[3] manufactured by Hankyu Kyoei Bussan Co., Ltd., Osaka, Japan As a result, it was confirmed that the two step reaction of the proteinase and the fraction 4 obtained in Experiment 4 can produce the tripeptides Ile-Pro-Pro and Val-Pro-Pro when "PROTEASE A™" (derived from *Aspergillus oryzae*, manufactured by Amano Pharmaceutical Co., Ltd), "PROTEASE M™" (derived from *Aspergillus oryzae*, manufactured by Amano Pharmaceutical Co., Ltd, Nagoya, Japan), and "PROTEASE P™" (derived from *Aspergillus melleus*, manufactured by Amano Pharmaceutical Co., Ltd., Nagoya, Japan) as well as papain was employed as the proteinase. The tripeptides Ile-Pro-Pro and Val-Pro-Pro were not obtained when other proteinase were employed.

Example 1

Production of the Tripeptide Val-Pro-Pro and Ile-Pro-Pro from Casein –1

50 mg of casein (product name "SUNLACT S™" manufactured by Taiyo Kagaku Co., Ltd., Yokkaichi, Japan) was dissolved in 10 ml of 50 mM phosphate buffer (pH 6.5), and admixed with 0.2 mg of papain (manufactured by Sigma Chemical Co., St. Louis, Mo.) The mixture was reacted at 37° C. for 12 hours. After finishing the reaction, the liquid was heated at 100° C. for 3 minutes and then rapidly cooled down for inactivating the enzyme. 10 ml of the reacted liquid was then passed through Sep-pak C18 Cartridge (manufactured by Waters Corporation). The adsorbed peptides were eluted with 5 ml of 30 vol % acetonitrile. Acetonitrile was distilled out of the fractions of the eluted peptide. The fraction was then dissolved in 1 ml of 50 mM tris-Cl (ph 8.0), admixed with 0.1 μg/ml each of aminopeptidase I (manufactured by Amano Pharmaceutical Co., Ltd. Nagoya, Japan) and carboxypeptidase Y (manufactured by Amano Pharmaceutical Co., Ltd., Nagoya, Japan) and reacted at 37° C. for 12 hours. After the reaction, the liquid was analyzed by the following HPLC procedure for quantifying the amount of the tripeptides Val-Pro-Pro and Ile-Pro-Pro.

(Quantification of Val-Pro-Pro and Ile-Pro-Pro by HPLC)

The sample was sequentially diluted with HPLC eluent (aqueous solution containing 0.3 M NaCl and 0.05 wt % TFA). Quantitative analysis was performed by measuring the height of the peak of the tripeptides Ile-Pro-Pro and Val-Pro-Pro using synthetic peptides as standard samples. HPLC conditions for the quantitative analysis was as follows:

Apparatus used: Hitachi L4000 UV detector (215 nm)
L6200 intelligent pump
L5030 column oven (35° C.)
Separating condition: flow rate; 0.5 ml/min.
Eluent: Aqueous solution containing 0.3 M NaCl and 0.05 wt % TFA
Column: Asahipak GS320 (φ3.9×600 mm) (manufactured by Showa Denko K. K.)

As a result, it was found that the reacted liquid contained 50 μg of the tripeptide Val-Pro-Pro and 50 μg of the tripeptide Ile-Pro-Pro per 50 mg of casein. Casein, particularly beta casein, includes one each of sequences Val-Pro-Pro and Ile-Pro-Pro. If the tripeptides Ile-Pro-Pro and Val-Pro-Pro are produced from 100% of these sequences, the theoretical amount of the tripeptide production is approximately 4 mg per 1 g of casein. Therefore, the yield of this experiment was calculated to be 25% for both tripeptides in accordance with the following equation:

Yield=(measured amount/theoretical amount)×100(%)

Val Pro Pro=0.05 mg/(4 mg×50 mg/1000 mg)×100(%)=25%

Ile Pro Pro=0.5 mg/(4 mg×50 mg/1000 mg)×100(%)=25%

Example 2

Production of the Tripeptide Val-Pro-Pro And Ile-Pro-Pro from Casein –2

50 mg of casein (product name "SUNLACT S™" manufactured by Taiyo Kagaku Co., Ltd. Yokkaichi, Japan) was dissolved in 10 ml of 50 mM phosphate buffer (pH 6.5), and admixed with 0.2 mg of papain. (manufactured by Sigma Chemical Co., St. Louis, Mo.). the mixture was reacted at 37° C. for 12 hours. After finishing the reaction, the liquid was heated at 100° C. for 3 minutes and then rapidly cooled to inactivate the enzyme. The liquid was then admixed with 1 ml of the purified enzyme fraction extracted from *Lactobacillus helveticus* obtained in Experiment 4 (the fraction 4) and reacted at 37° C. for 12 hours. The reacted liquid contained 50 μg of the tripeptide Val-Pro-Pro (yield 25%) and 50 μg of the tripeptide Ile-Pro-Pro (yield 25%) per 50 mg of casein.

Example 3

Production of the Tripeptide Val-Pro-Pro and Ile-Pro-Pro from Casein –3

50 mg of casein (product name "Sunlact S" manufactured by Taiyo Kagaku Co., Ltd.) was dissolved in 10 ml of 50 mM phosphate buffer (pH 6.5), and admixed with 0.2 mg of papain (manufactured by Sigma Chemical Co.). The mixture was reacted at 37° C. for 12 hours. After finishing the reaction, the liquid was heated at 100° C. for 3 minutes and then rapidly cooled down for inactivating the enzyme. The liquid was then admixed with 1 ml of the purified enzyme fraction extracted from *Lactobacillus helveticus* obtained in Experiment 4 (the fraction 4) and reacted at 37° C. for 12 hours. The reacted liquid contained 50 μg of the tripeptide Val-Pro-Pro (yield 25%) and 50 μg of the tripeptide Ile-Pro-Pro (yield 25%) per 50 mg of casein.

Examples 4–6

Production of the Tripeptide Val-Pro-Pro and Ile-Pro-Pro from Casein –4

150 mg of casein (product name "SUNLACT S™" manufactured by Taiyo Kagaku Co., Ltd., Yokkaichi, Japan) was dissolved in 30 ml of 50 mM phosphate buffer (pH 6.5). The mixture was divided into 10 ml aliquots. Each of the aliquots was admixed with 0.2 mg of one of the "PROTEASE A™" (Example 4) "PROTEASE M™" (Example 5) and "PROTEASE P™" (Example 6) (product names, manufacture by Amano Pharmaceutical Co., Ltd., Nagoya, Japan). The mixture was reacted at 37° C. for 12 hours. After finishing the reaction, the liquid was heated at 100° C. for 3 minutes and then rapidly cooled to inactivate the enzyme. The liquid was then admixed with 1 ml of the purified enzyme fraction extracted from *Lactobacillus helveticus* obtained in Experiment 4 (the fraction 4) and reacted at 37° C. for 12 hours. The contents of the tripeptides Val-Pro-Pro and Ile-Pro-Pro per 50 mg of casein in the reacted liquid were 40 μg (yield 20%) and 45 μg (yield 22.5%), respectively, in Example 4, 37 μg (yield 18.5%) and 50 μg (yield 25%), respectively, in Example 5, and 42 μg (yield 21%) and 45 μg (yield 22.5%), respectively, in Example 6.

What is claimed is:

1. A method for producing a tripeptide by digesting a material containing a milk casein with a proteinase and a peptidase to obtain at least one of Val-Pro-Pro and Ile-Pro-Pro, said method comprising the steps of digesting said material containing said milk casein with said proteinase to produce an intermediate peptide selected from the group consisting of a peptide containing the sequence Val-Pro-Pro but containing no Pro other than those in Val-Pro-Pro, a peptide containing the sequence Ile-Pro-Pro but containing no Pro other than those in Ile-Pro-Pro, and mixtures thereof, and digesting said intermediate peptide with said peptidase to produce at least one of Val-Pro-Pro and Ile-Pro-Pro.

2. The method of claim 1 wherein said proteinase is selected from the group consisting of papain, a protease obtained from *Aspergillus oryzae*, a protease obtained from *Aspergillus melleus* and mixtures thereof.

3. The method of claim 1 wherein said intermediate peptide is selected from the group consisting of those represented by SEQ ID NO: 1 to SEQ ID NO: 27 and mixtures thereof.

4. The method of claim 1 wherein said peptidase is selected from the group consisting of an amino peptidase, a carboxypeptidase, an oligopeptidase and mixtures thereof.

5. The method of claim 1 wherein said peptidase contains a peptidase that is at least one of a carboxypeptidase and an oligopeptidase capable of cleaving a bond between Pro and Xaa of at least one of the sequences Val-Pro-Pro-Xaa and Ile-Pro-Pro-Xaa; wherein Xaa represents any amino acid.

6. The method of claim 1 wherein said peptidase is derived from *Lactobacillus helveticus*.

7. The method of claim 6 wherein said *Lactobacillus helveticus* is FERM BP-6060.

8. The method of claim 1, said method further comprising the step of elevating concentrations of said intermediate peptide using a hydrophobic resin after digesting said material containing said milk casein with said proteinase to produce said intermediate peptide and before performing said digestion with said peptidase.

9. The method of claim 2, wherein the protease obtained from *Aspergillus oryzae* is enzymatically stable at a neutral pH.

10. The method of claim 2, wherein the protease obtained from *Aspergillus oryzae* is enzymatically stable at an acidic pH.

11. The method of claim 2, wherein the protease obtained from *Aspergillus melleus* is enzymatically stable at a neutral pH.

12. The method of claim 9, wherein the protease obtained from *Aspergillus oryaze* has a protease activity of not less than 10,000 units/g at a pH of 7.0, according to the Amano method.

13. The method of claim 10, wherein the protease obtained from *Aspergillus oryzae* has a protease activity of not less than 5,500 unts/g at a pH of 3.0, measured according to the Amano method.

14. The method of claim 11, wherein the protease obtained from *Aspergillus melleus* has a protease activity of not less than 30,000 units/g at a pH of 8.0, measured according to the Amano method.

* * * * *

UNITED STATES PATENT AND TRADEMARK OFFICE
CERTIFICATE OF CORRECTION

PATENT NO. : 6,994,987 B1 Page 1 of 1
DATED : February 7, 2006
INVENTOR(S) : Naoyuki Yamamoto et al.

It is certified that error appears in the above-identified patent and that said Letters Patent is hereby corrected as shown below:

<u>Title page,</u>
Item [75], Inventors, delete "Keita Ueno, Machida (JP)" and substitute -- Keita Ueno, Kanagawa, Japan --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,994,987 B1 | Page 1 of 1 |
| APPLICATION NO. | : 10/129471 | |
| DATED | : February 7, 2006 | |
| INVENTOR(S) | : Naoyuki Yamamoto | |

It is certified that error appears in the above-identified patent and that said Letters Patent is hereby corrected as shown below:

Column 12, line 35 - delete "the" and insert -- The --

Column 12, line 38 - delete "to inactivate the enzyme. The liquid" and insert -- down for inactivating the enzyme. 10 ml of the reacted liquid was then passed through Sep-pak C18 Cartridge (manufactured by Waters Corporation). The adsorbed peptides were eluted peptide. The fraction with 5ml of 30 vol% acetonitrile. Acetonitrile was distilled out of the fractions of the eluted --

Column 12, line 43 - delete "50 μg" and insert -- 195 μg --

Column 12, line 43 - delete "25%" and insert -- 97.5%--

Column 12, line 49 - delete "Sunlact S" and insert -- SUNLACT S™ --

Column 12, line 50 - after Taiyo Kagaku Co., Ltd. insert --, Yokkaichi, Japan --

Column 12, line 52 - after Sigma Chemical Co. insert --, St. Louis, MO --

Column 12, line 55 - delete "down for inactivating" and insert -- to inactivate --

Signed and Sealed this
Twenty-fifth Day of January, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 6,994,987 B1 |
| APPLICATION NO. | : 10/129471 |
| DATED | : February 7, 2006 |
| INVENTOR(S) | : Naoyuki Yamamoto, Keita Ueno and Masahiro Ejiri |

It is certified that error appears in the above-identified patent and that said Letters Patent is hereby corrected as shown below:

Column 12, line 38 - delete "to inactivate the enzyme. The liquid" and insert -- down for inactivating the enzyme. 10 ml of the reacted liquid was then passed through Sep-pak C18 Cartridge (manufactured by Waters Corporation). The adsorbed peptides were eluted with 5ml of 30 vol% acetonitrile. Acetonitrile was distilled out of the fractions of the eluted peptide. The fraction --

Signed and Sealed this
Twenty-eighth Day of June, 2011

David J. Kappos
*Director of the United States Patent and Trademark Office*

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Gln Asn Ile Pro Pro Leu Thr Gln Thr
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic peptide

<400> SEQUENCE: 2

Asn Ile Pro Pro Leu Thr Gln Thr
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic peptide

<400> SEQUENCE: 3

Ile Pro Pro Leu Thr Gln Thr
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic peptide

<400> SEQUENCE: 4

Gln Asn Ile Pro Pro Leu Thr Gln
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Asn Ile Pro Pro Leu Thr Gln
```

```
<210> SEQ ID NO 6
<211> LENGTH: 6
<212> TYPE: PRT
<213> ORGANISM: Artificial Sequence
<220> FEATURE:
<223> OTHER INFORMATION: synthetic peptide

<400> SEQUENCE: 6

Ile Pro Pro Leu Thr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic peptide

<400> SEQUENCE: 7

Gln Asn Ile Pro Pro Leu Thr
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide

<400> SEQUENCE: 8

Asn Ile Pro Pro Leu Thr
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic peptide

<400> SEQUENCE: 9

Ile Pro Pro Leu Thr
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide

<400> SEQUENCE: 10

Gln Asn Ile Pro Pro Leu
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic sequence

<400> SEQUENCE: 11

Asn Ile Pro Pro Leu
1               5
```

```
<210> SEQ ID NO 12
<211> LENGTH: 4
<212> TYPE: PRT
<213> ORGANISM: Artificial Sequence
<220> FEATURE:
<223> OTHER INFORMATION: synthetic peptide

<400> SEQUENCE: 12

Ile Pro Pro Leu
1

<210> SEQ ID NO 13
<211> LENGTH: 5
<212> TYPE: PRT
<213> ORGANISM: Artificial Sequence
<220> FEATURE:
<223> OTHER INFORMATION: synthetic peptide

<400> SEQUENCE: 13

Gln Asn Ile Pro Pro
1               5

<210> SEQ ID NO 14
<211> LENGTH: 4
<212> TYPE: PRT
<213> ORGANISM: Artificial Sequence
<220> FEATURE:
<223> OTHER INFORMATION: synthetic peptide

<400> SEQUENCE: 14

Asn Ile Pro Pro
1

<210> SEQ ID NO 15
<211> LENGTH: 3
<212> TYPE: PRT
<213> ORGANISM: Artificial Sequence
<220> FEATURE:
<223> OTHER INFORMATION: synthetic peptide

<400> SEQUENCE: 15

Ile Pro Pro
1

<210> SEQ ID NO 16
<211> LENGTH: 8
<212> TYPE: PRT
<213> ORGANISM: Artificial Sequence
<220> FEATURE:
<223> OTHER INFORMATION: synthetic peptide

<400> SEQUENCE: 16

Val Val Val Pro Pro Phe Leu Gln
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic peptide

<400> SEQUENCE: 17

Val Val Pro Pro Phe Leu Gln
1               5
```

-continued

```
<210> SEQ ID NO 18
<211> LENGTH: 6
<212> TYPE: PRT
<213> ORGANISM: Artificial Sequence
<220> FEATURE:
<223> OTHER INFORMATION: synthetic peptide

<400> SEQUENCE: 18

Val Pro Pro Phe Leu Gln
 1               5

<210> SEQ ID NO 19
<211> LENGTH: 7
<212> TYPE: PRT
<213> ORGANISM: Artificial Sequence
<220> FEATURE:
<223> OTHER INFORMATION: synthetic peptide

<400> SEQUENCE: 19

Val Val Val Pro Pro Phe Leu
 1               5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide

<400> SEQUENCE: 20

Val Val Pro Pro Phe Leu
 1               5

<210> SEQ ID NO 21
<211> LENGTH: 5
<212> TYPE: PRT
<213> ORGANISM: Artificial Sequence
<220> FEATURE:
<223> OTHER INFORMATION: synthetic peptide

<400> SEQUENCE: 21

Val Pro Pro Phe Leu
 1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide

<400> SEQUENCE: 22

Val Val Val Pro Pro Phe
 1               5

<210> SEQ ID NO 23
<211> LENGTH: 5
<212> TYPE: PRT
<213> ORGANISM: Artificial Sequence
<220> FEATURE:
<223> OTHER INFORMATION: synthetic peptide

<400> SEQUENCE: 23

Val Val Pro Pro Phe
 1               5
```

-continued

```
<210> SEQ ID NO 24
<211> LENGTH: 4
<212> TYPE: PRT
<213> ORGANISM: Artificial Sequence
<220> FEATURE:
<223> OTHER INFORMATION: synthetic peptide

<400> SEQUENCE: 24

Val Pro Pro Phe
1

<210> SEQ ID NO 25
<211> LENGTH: 5
<212> TYPE: PRT
<213> ORGANISM: Artificial Sequence
<220> FEATURE:
<223> OTHER INFORMATION: synthetic peptide

<400> SEQUENCE: 25

Val Val Val Pro Pro
1               5

<210> SEQ ID NO 26
<211> LENGTH: 4
<212> TYPE: PRT
<213> ORGANISM: Artificial Sequence
<220> FEATURE:
<223> OTHER INFORMATION: synthetic peptide

<400> SEQUENCE: 26

Val Val Pro Pro
1

<210> SEQ ID NO 27
<211> LENGTH: 3
<212> TYPE: PRT
<213> ORGANISM: Artificial Sequence
<220> FEATURE:
<223> OTHER INFORMATION: synthetic peptide

<400> SEQUENCE: 27

Val Pro Pro
1

<210> SEQ ID NO 28
<211> LENGTH: 28
<212> TYPE: PRT
<213> ORGANISM: Artificial Sequence
<220> FEATURE:
<223> OTHER INFORMATION: synthetic peptide

<400> SEQUENCE: 28

Leu Pro Gln Asn Ile Pro Pro Leu Thr Gln Thr Pro Val Val Val Pro
1               5                   10                  15
Pro Phe Leu Gln Pro Glu Val Met Gly Val Ser Lys
            20                  25

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Val Pro Pro Phe Leu Gln Pro Glu
1               5
```